(12) United States Patent
Abdelgany

(10) Patent No.: US 7,967,848 B2
(45) Date of Patent: Jun. 28, 2011

(54) SPRING-LOADED DYNAMIC PEDICLE SCREW ASSEMBLY

(75) Inventor: Mahmoud F. Abdelgany, Rockaway, NJ (US)

(73) Assignee: Custom Spine, Inc., Parsippany, NJ (US)

(*) Notice: Subject to any disclaimer, the term of this patent is extended or adjusted under 35 U.S.C. 154(b) by 800 days.

(21) Appl. No.: 12/015,028

(22) Filed: Jan. 16, 2008

(65) Prior Publication Data
US 2009/0182380 A1 Jul. 16, 2009

(51) Int. Cl.
*A61B 17/70* (2006.01)
(52) U.S. Cl. ......... 606/266; 606/267; 606/270; 606/306
(58) Field of Classification Search .................... 606/60, 606/246, 254, 255, 257, 260, 264–268, 270, 606/273–278
See application file for complete search history.

(56) References Cited

U.S. PATENT DOCUMENTS

| | | | |
|---|---|---|---|
| 5,259,398 A | 11/1993 | Vrespa | |
| 5,474,555 A | 12/1995 | Puno et al. | |
| 6,471,705 B1 | 10/2002 | Biedermann et al. | |
| 7,766,915 B2 * | 8/2010 | Jackson | 606/86 A |
| 7,857,834 B2 * | 12/2010 | Boschert | 606/269 |
| 7,862,586 B2 * | 1/2011 | Malek | 606/246 |
| 2003/0176861 A1 * | 9/2003 | Reed | 606/61 |
| 2005/0192571 A1 * | 9/2005 | Abdelgany | 606/61 |
| 2005/0277928 A1 * | 12/2005 | Boschert | 606/61 |
| 2007/0093832 A1 | 4/2007 | Abdelgany | |
| 2010/0137911 A1 * | 6/2010 | Dant | 606/252 |

* cited by examiner

*Primary Examiner* — Eduardo C Robert
*Assistant Examiner* — Ellen C Hammond
(74) *Attorney, Agent, or Firm* — Rahman LLC

(57) ABSTRACT

An assembly that includes a fixator component, a clamping mechanism, a screw head, a load sharing mechanism, and a blocker. The fixator component further includes a bulbous end, a neck portion, and a threaded end. The clamping mechanism is positioned around the neck portion of the fixator component. The load sharing mechanism is positioned in between the screw head and the bone fixator component. The screw head further includes a pair of diametrically opposed arms, a socket and a slot. The socket is positioned between the pair of arms and the slot is positioned above the socket. The socket is dimensioned and configured to house the bulbous end of the fixator component. The load sharing mechanism provides tensile resistance to the screw head and the blocker is adapted to engage the screw head.

20 Claims, 16 Drawing Sheets

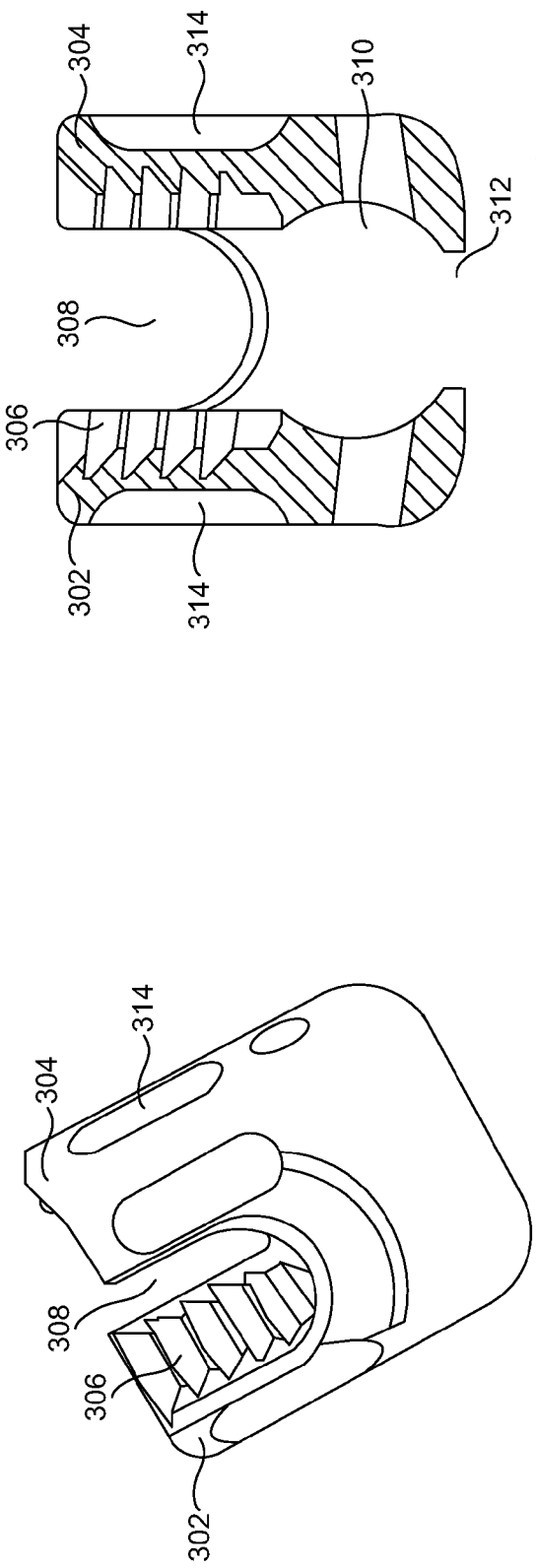
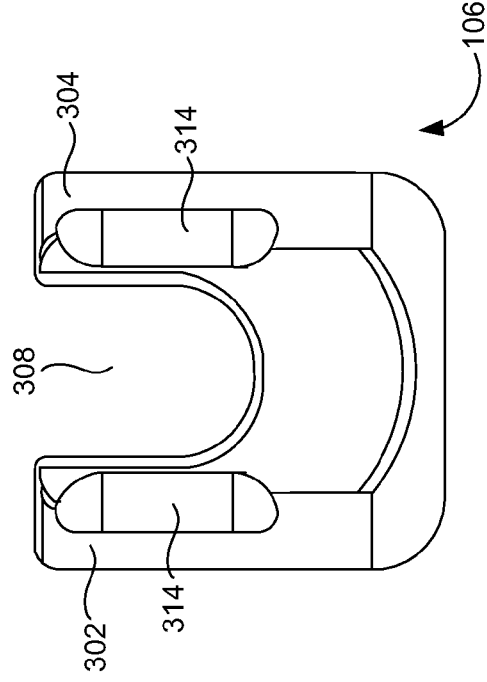
FIG. 3A
FIG. 3B
FIG. 3C

SPRING-LOADED DYNAMIC PEDICLE SCREW ASSEMBLY

BACKGROUND

1. Technical Field

The embodiments herein generally relate to medical devices and assemblies, and more particularly to an orthopedic spring-loaded dynamic pedicle screw assembly used for surgical lumbar, thoracic, and cervical spine treatment.

2. Description of the Related Art

Surgical procedures treating spinal injuries are one of the most complex and challenging surgeries for both the patient and the surgeon. A common problem with the internal spinal fusion is how to secure the fixation devices without damaging the spinal cord. The pedicles are a favored area of attachment since they offer an area that is strong enough to hold the fixation device even when the patient suffers from osteoporosis (e.g., a disease of bone leading to an increased risk of fracture).

More recently, methods of internal fixation have utilized wires that extend through the spinal canal and hold a rod against lamina or that utilize pedicle screws, which extend into the pedicle and secure a plate, which extends across several vertebral segments. However, the wired implants include an increased risk of damage to the neural elements (e.g., spinal cord and nerve roots). On the other hand, the use of plates with the screws rigidly linked results in the direct transfer of loads at the bone screw interface, which is the weakest link in the fixation spine construction. This can result in breakage of the screw or failure of the bone screw interface prior to achieving fusion. In addition, the plate designs are generally bulky and tend to leave little surface for bone grafting and they typically cannot be easily contoured to account for the lateral curvature of the spine.

Additionally, some methods have used polyaxial screw systems for fixation. Conventional polyaxial screw systems typically consist of a screw-receiving portion with the bottom portion of the screw-receiving portion pivoting inside a bone screw, and a receiving rod. This typical conventional design necessitates the screw-receiving portion to have a narrow neck just above the entrance to the screw. This smaller and weaker neck portion is significantly further away from the forces being applied through the rod, which consequently allows a bigger moment arm and increases the chance of breakage at the weak neck portion.

Furthermore, most conventional screw assemblies generally do not allow for a bone screw to be tensioned in a given zone or range of angulations in the screw head. Consequentially, most conventional solutions use the rod portion of the system to provide the dynamism. Generally, most artificial discs currently being marketed do not typically offer any resistance at the extreme ranges of motion, and others tend to offer a "dead stop" that may cause implant failure or implant dislodging. As such, most surgeons would concede that the removal of a failed artificial disc is an extremely undesirable event that is fraught with major complications.

Moreover, when there are various deformities, trauma, or fractures of the vertebra, due to the complexity of the human anatomy, surgeons may attempt to "fuse" the vertebrae by bending the rod (causing notches thereby reducing fatigue resistance) before placing them into two or more non-aligned pedicle screws in order to properly stabilize the pedicle screw assembly within the patient's body.

Furthermore, most conventional screw receiving portions do not generally offer enough medial-lateral flexibility because the rod sits too closely on top of the center of rotation of the bone screw producing a smaller arc of rotation. Moreover, most conventional screw systems do not generally accommodate different rod sizes. Additionally, most conventional spinal implant designs typically lack features that enhance invasive surgery techniques that are used for spinal surgeries which can decrease the patient's recovery time. Also, there is generally a lack of limitation of load sharing ability, which may lead to damage of the vertebrae during natural motion. Thus, there remains a need for a new and improved dynamic pedicle screw assembly with intra-operative flexibility, that allows the bone screw to be tensioned in a given zone or range of angulations in the screw head while permitting natural motion.

SUMMARY

In view of the foregoing, an embodiment herein provides a new and improved dynamic pedicle screw assembly with intra-operative flexibility, that allows the bone screw to be tensioned in a given zone or range of angulations in the screw head while permitting natural motion. The dynamic pedicle screw assembly includes a fixator component, a clamping mechanism, a screw head, a load sharing mechanism, and a blocker. The fixator component further includes a bulbous end, a neck portion, and a threaded end.

The clamping mechanism is positioned around the neck portion of the fixator component. The clamping mechanism may include a width greater than a width of the bulbous end of the fixator component. The load sharing mechanism may include a slot and is positioned in between the screw head and the bone fixator component. The load sharing mechanism may include any of a wave washer, a collapsible hollow washer, a coiled spring, and a flexible washer. The load sharing mechanism provides tensile resistance to the screw head. The blocker is adapted to engage the screw head.

The screw head further includes a pair of diametrically opposed arms, a socket and a slot. The socket is positioned between the pair of arms and the slot is positioned above the socket. The socket is dimensioned and configured to house the bulbous end of the fixator component. The slot may be dimensioned and configured for receiving a longitudinal member. The fixator component may include a bone screw and a hook and may be spaced apart from the longitudinal member.

In another aspect, a pedicle fixation assembly includes a bone screw, a shoulder mechanism, a screw head, a load sharing mechanism, and a threaded blocker mechanism. The bone screw further includes a bulbous end, a neck portion, and a threaded end. The shoulder mechanism is positioned around the neck portion of the bone screw and may be detachable. The shoulder mechanism may include a width equal to a width of the bulbous end of the bone screw. The load sharing mechanism is positioned in between the screw head and the bone screw. The load sharing mechanism may include a slot to allow the load sharing mechanism to snap onto the neck portion of the bone screw. The load sharing mechanism may include any of a wave washer, a collapsible hollow washer, a coiled spring, and a flexible washer.

The screw head further includes a pair of threaded upright arms, a socket, a slot, and a hole adjacent to the socket. The socket is positioned between the pair of arms. The slot is positioned at a first end of the screw head and between the pair of arms. The hole is positioned at a second end of the screw head. The socket is dimensioned and configured to house the bulbous end of the bone screw. The slot may be dimensioned and configured for receiving a longitudinal member. The bone screw may be spaced apart from the longitudinal member. The load sharing mechanism provides tensile resistance to the screw head and the threaded blocker mechanism is adapted to engage the threads of the pair of arm of the screw head.

In yet another aspect, an apparatus includes a bone screw, a shank structure, a screw head, a load sharing mechanism, a longitudinal member, and a threaded blocker mechanism. The bone screw further includes a bulbous end, a neck portion, and a threaded end. The shank structure is positioned around the neck portion of the bone screw and includes a width at least equal to a width of the bulbous end of the bone screw. The screw head further includes a pair of threaded upright arms, a socket, a slot, and a hole adjacent to the socket. The socket is positioned between the pair of arms. The slot is positioned at a first end of the screw head and between the pair of arms. The hole is positioned at a second end of the screw head. The socket is dimensioned and configured to house the bulbous end of the bone screw. The longitudinal member is positioned in the slot of the screw head.

The load sharing mechanism is positioned in between the screw head and the bone screw and provides tensile resistance to the screw head. The load sharing mechanism may include any of a wave washer, a collapsible hollow washer, a coiled spring, and a flexible washer. The load sharing mechanism may include a slot to allow the load sharing mechanism to snap onto the neck portion of the bone screw. The threaded blocker mechanism is adapted to engage the threads of the pair of arm of the screw head and secure the longitudinal member in the slot. The bone screw may not contact the longitudinal member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 3A through 3C illustrate a perspective view, a cross-sectional view, and a front view, respectively, of a screw head of the screw assembly of FIG. 1 according to the embodiments herein;

DETAILED DESCRIPTION OF PREFERRED EMBODIMENTS

Figure 1:
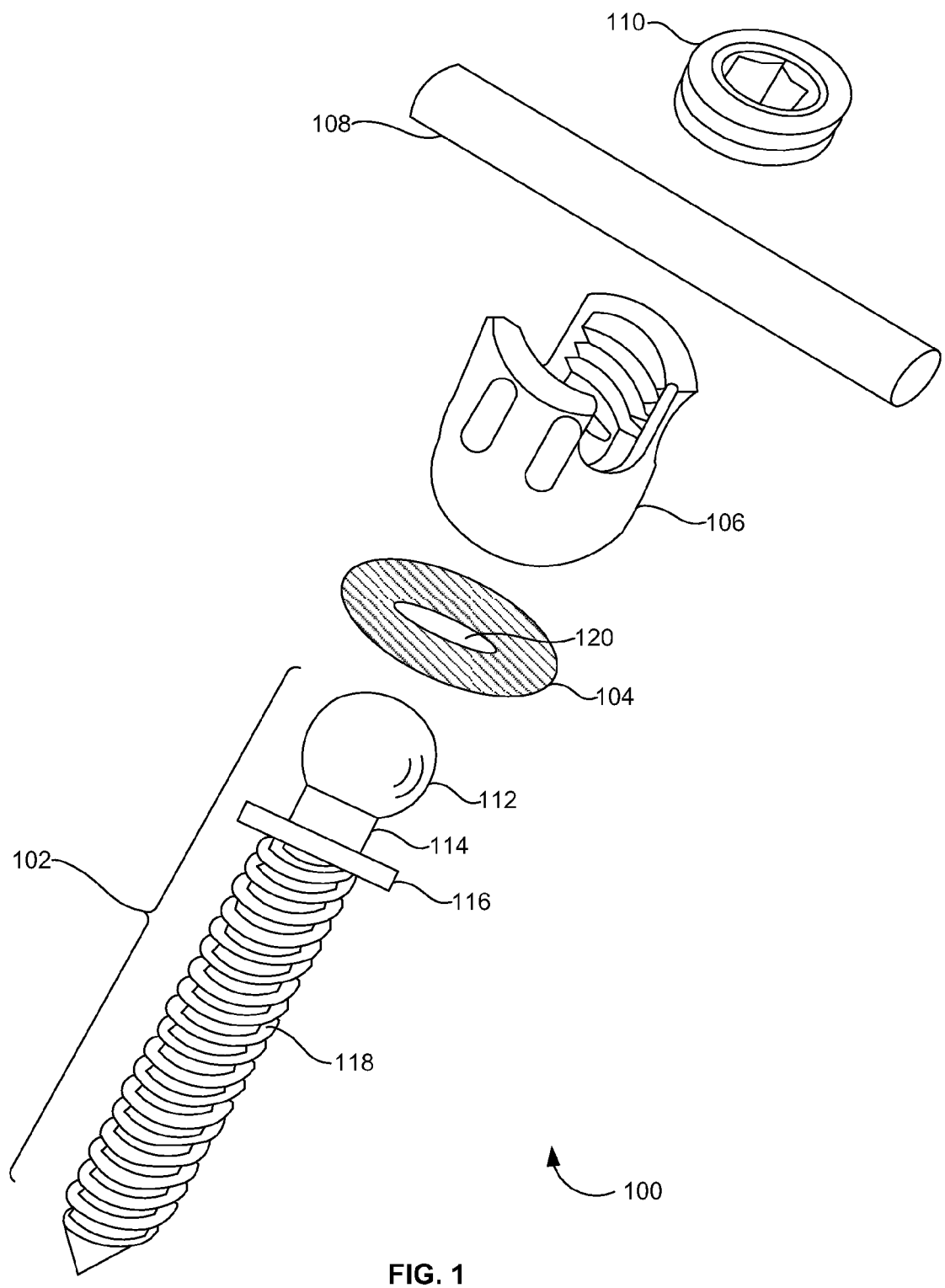
FIG. 1 illustrates an exploded view of a screw assembly according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new and improved dynamic pedicle screw assembly with intra operative flexibility, that allows the bone screw to be tensioned in a given zone or range of angulations in the screw head while permitting natural motion. The embodiments herein address this need by providing an assembly 100 that includes a fixator component 102, a clamping mechanism 116, a screw head 106, a load sharing mechanism 104, and a blocker 110. The fixator component 102 further includes a bulbous end 112, a neck portion 114, and a threaded end 118. The clamping mechanism 116 is positioned around the neck portion 114 of the fixator component 102. The load sharing mechanism 104 is positioned in between the screw head 106 and the fixator component 102. The screw head 106 further includes a pair of diametrically opposed arms 302, 304, a socket 310, and a slot 308. The socket 310 is positioned between the pair of arms 302, 304, and the slot 308 is positioned above the socket 310. The socket 310 is dimensioned and configured to house the bulbous end 112 of the fixator component 102. The load sharing mechanism 104 provides tensile resistance to the screw head 106 and the blocker 110 is adapted to engage the screw head 106. Referring now to the drawings and more particularly to FIGS. 1 through 10 where similar reference characters denote corresponding features consistently throughout the figures, there are shown preferred embodiments.

Figure 2A:
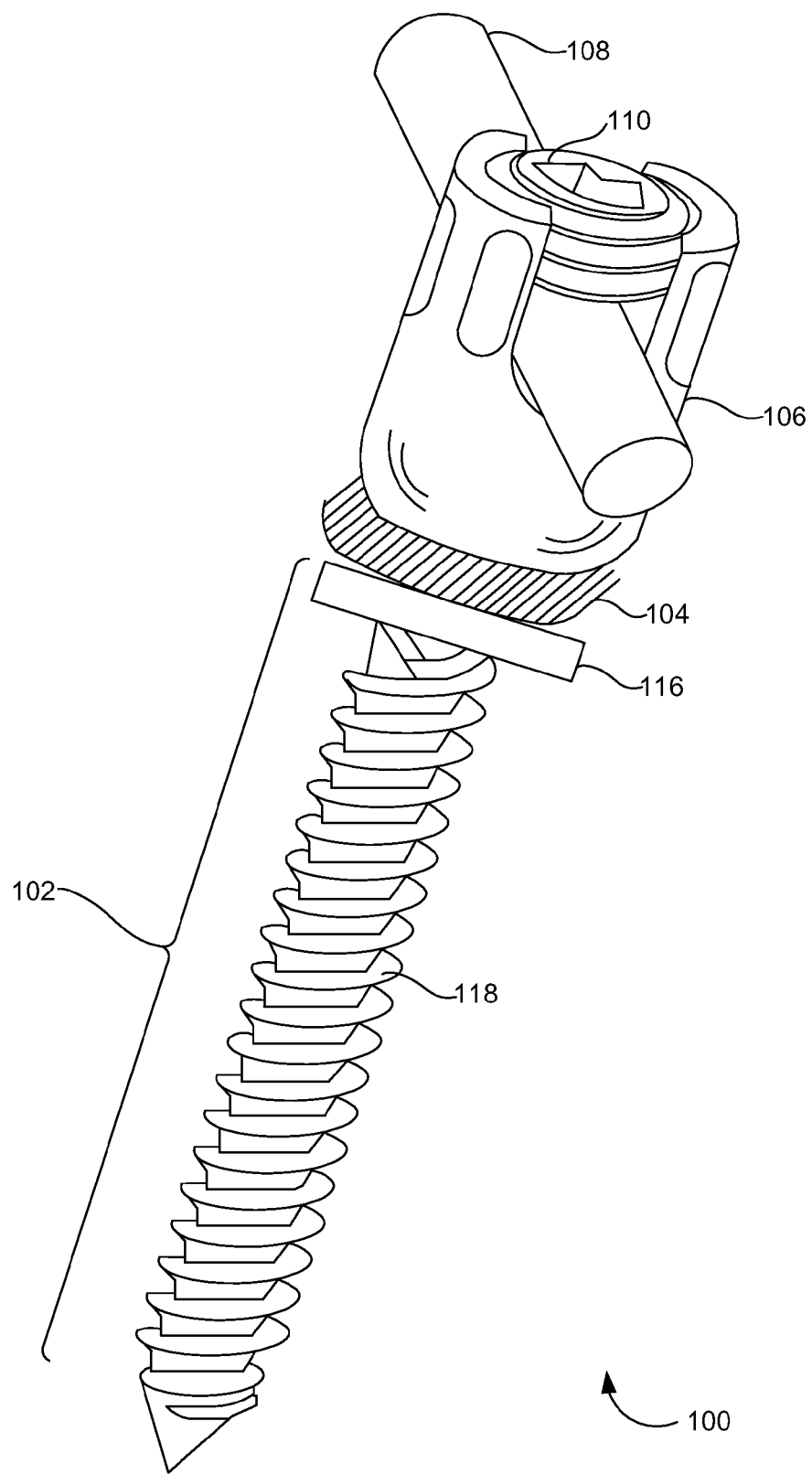
FIG. 2A illustrates an assembled view of the screw assembly of FIG. 1 according to the embodiments herein.
Figure 2B:
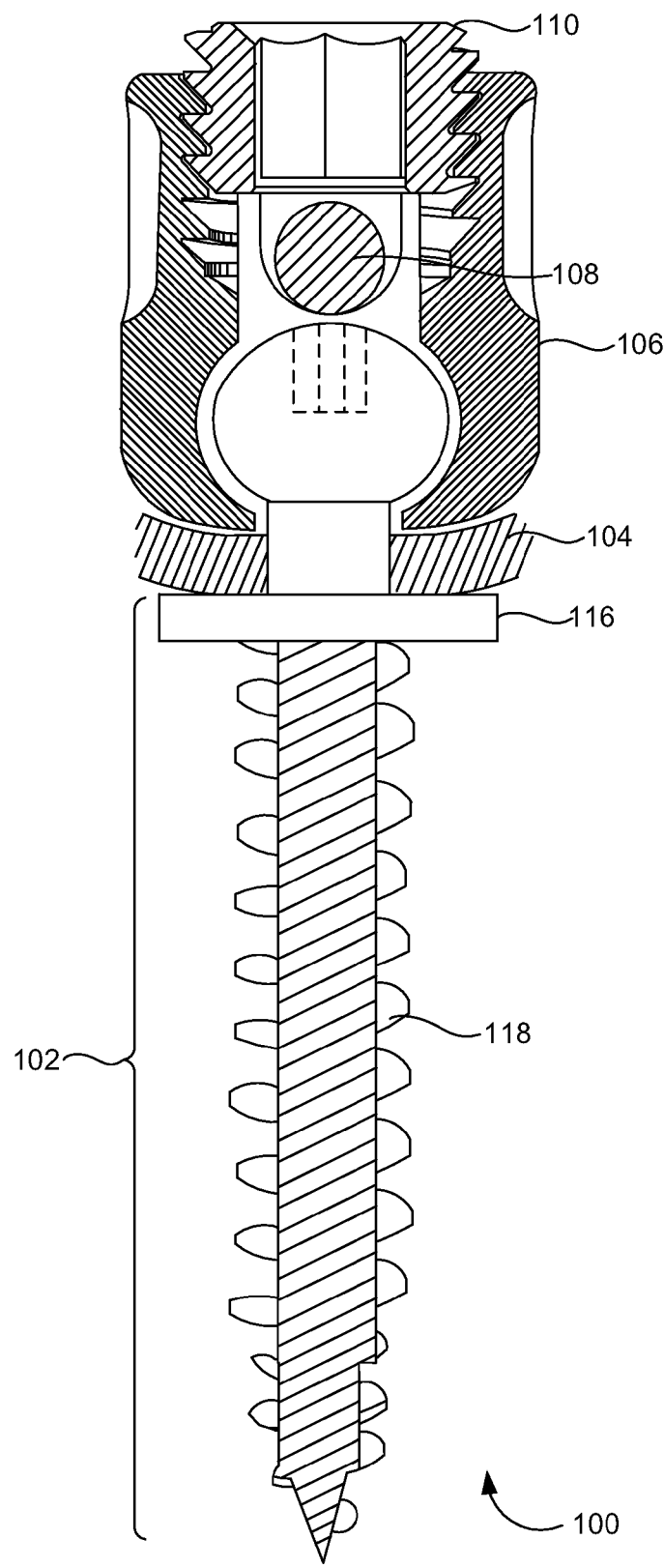
FIG. 2B illustrates a cross-sectional view of the screw assembly of FIG. 2A according to the embodiments herein.

With reference to FIGS. 1 through 2B, the screw assembly 100 includes a bone fixator component 102, a load sharing mechanism 104, a screw head 106, a longitudinal member 108, and a blocker 110. The bone fixator component 102 further includes a bulbous end 112, a neck portion 114, a clamping mechanism 116, and a threaded end 118. The load sharing mechanism 104 further includes a slot 120.

Figure 9A:
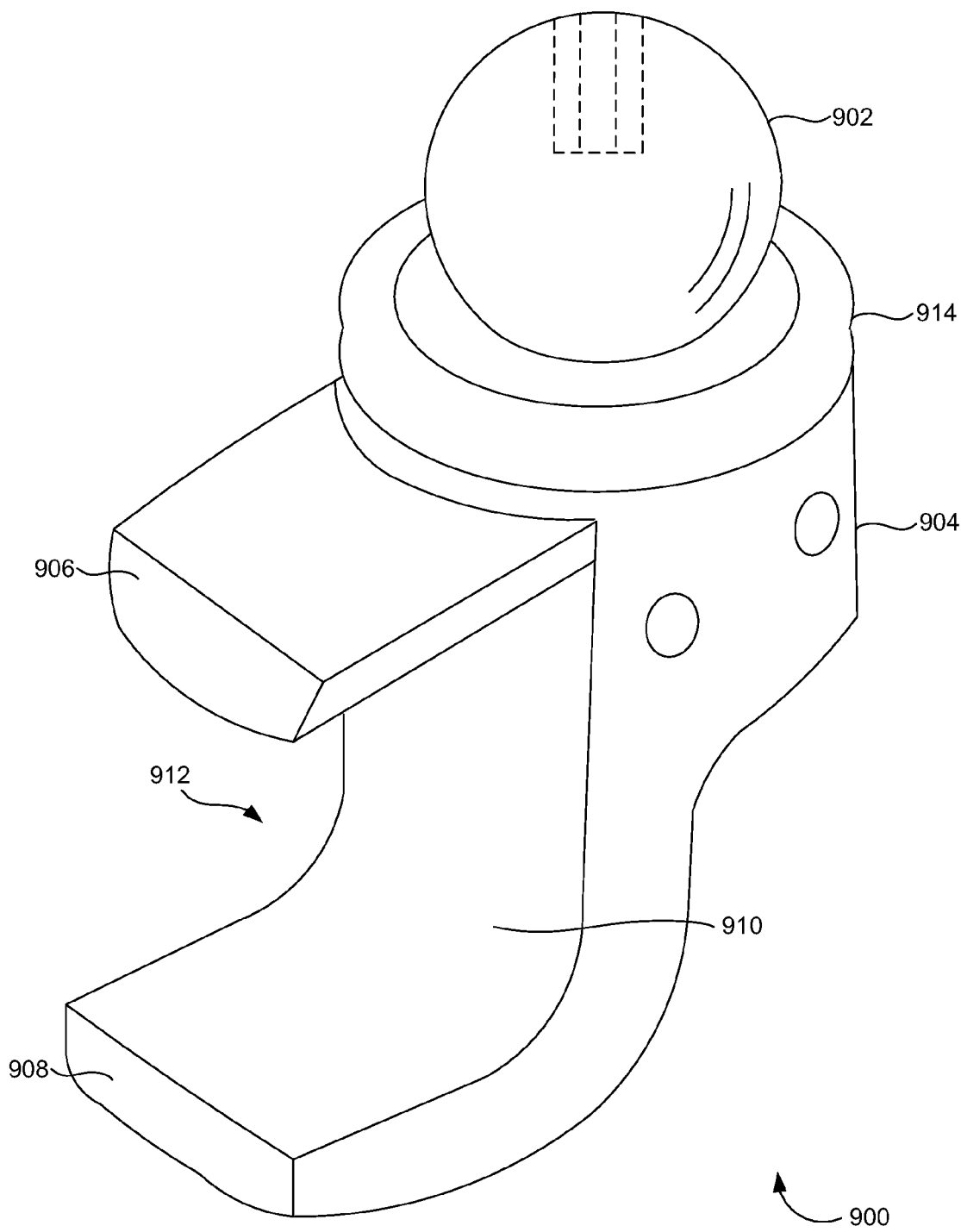
FIG. 9A illustrates a perspective view of a hook according to an alternate embodiment herein.
Figure 9B:
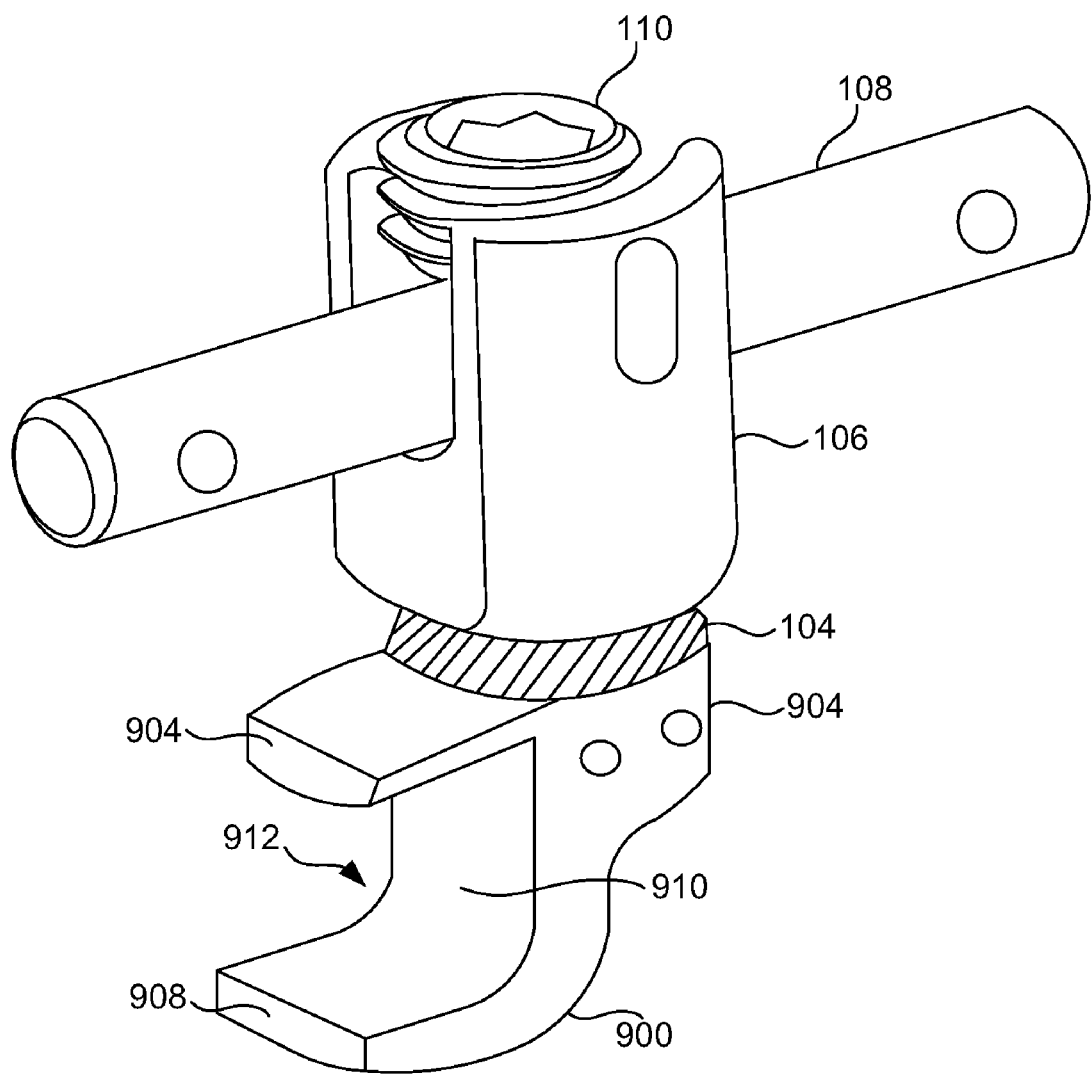
FIG. 9B illustrates a perspective view of the screw assembly according to the alternate embodiment herein.

The bone fixator component 102 is preferably configured as a bone screw, but alternatively, it may be configured as a hook 900 (best shown in FIGS. 9A and 9B). The bulbous end 112 of the bone screw 102 is adapted to be inserted in the screw head 106 (as illustrated in FIGS. 2A and 2B). The clamping mechanism 116 (may also be configured as a shoulder or a shank structure) is positioned around the neck portion 114 of the bone fixator component 102. The shoulder 116 comprises a width greater than or equal to a width of the bulbous end 112 of the bone screw 102. The shoulder 116 may be detachable and may have threads like a nut that screws onto the threads 118 of the bone screw 102, or the shoulder 116 can snap on the bone screw 102 like a C-ring, or the shoulder 116 can be welded onto the screw assembly 100. The thread 118 may be tapered on the minor diameter while cylindrical on the major diameter to allow a new "bite" with every turn and to accommodate more thread depth towards the bottom of the bone screw 102 for the cancellous bone. Furthermore, the threaded end 118 of the bone screw 102 may be a multiple lead thread to allow faster insertion into a bone. Additionally, the threads 118 of the bone screw 102 are preferably double lead, which provides greater surface contact with the bone, but drives at four mm/revolution. Moreover, since the bone screw 102 can be pivoted inside the socket 310 of the screw head 106, the screw assembly 100 is allowed to be inserted into the bone without having the bone or anatomy prematurely limit the range of angulations of the bone screw 102.

As implemented, the load sharing mechanism 104 is positioned between the bone screw 102 and the screw head 106 (as illustrated in FIGS. 2A and 2B). The load sharing mechanism 104 may be configured in different suitable configurations (best shown in FIGS. 5A through 8B). Preferably, the spring load sharing mechanism 104 can also have a minimal slot 120 to snap on the neck portion 114 of the bone screw 102 (as shown in FIG. 1). The load sharing mechanism 104 provides tensile resistance to the screw head 106. The screw head 106 (best shown in FIGS. 3A through 3C) is dimensioned and configured to accommodate the bulbous end 112 of the bone screw 102.

Once the bone screw 102 is inserted into the bone, a longitudinal member 108, which may be embodied as a rod, bar, etc., and the blocker 110 are inserted into the screw head 106 of the screw assembly 100. The rod 108 is generally comprised of a one-quarter inch stainless steel rod but could be made of any material which has suitable biocompatibility and material strength characteristics. The rod 108 should be able to withstand lateral bending forces and torsion since the system may be used to correct spinal displacement and curvature. On the other hand, it is important that the rod 108 can be bent to a certain extent so that the rod 108 can be bent to the proper curvature for the individual application. The bone screw 102 is spaced apart form the rod 108. The screw head 106 can accommodate 5.5 mm as well as 6.0 mm rods, which is advantageous over some conventional screw assemblies that are limited to accepting only rods of a uniform dimension. The blocker 110 is adapted to engage the screw head 106.

The screw assembly 100 comprises a ball and socket dynamic screw system that is sprung loaded or tensioned through the bone screw 102. The screw assembly 100 has many uses and may be used in various configurations of fixed, polyaxial, and dynamic screw systems including a micromotion fusion adjunct system that provides load sharing and helps avoid adjacent disc disease; a facet replacement system by providing torsional, axial, flexion, and extension ranges of motion; a load sharing and motion limiting system to complement a discectomy and postpone a fusion for several years; and a load sharing and motion limiting system to complement many of the conventional artificial discs currently being marketed and possibly being marketed in the future. The screw assembly 100 can also be configured in a rotationally articulated position.

As illustrated in FIGS. 3A through 3C, the screw head 106 includes a pair of upright arms 302, 304 comprising a threaded inner portion 306, a generally open U-shaped slot 308, a socket 310, a hole 312 positioned adjacent to the socket 310, and external cuts 314. The upright arms 302, 304 are diametrically opposed and separated by the U-shaped slot 308. The socket 310 is also positioned between the arms 302, 304. The U-shaped slot 308 is positioned at a first end of the screw head 106 and is positioned above the socket 310. The hole 312 is positioned at a second end of the screw head 106.

The arms 302, 304 with the threaded inner portion 306 are adapted to engage the blocker 110. The threaded inner portion 306 may be patterned in any suitable configuration and is adapted for engaging the blocker 110. The open U-shaped slot 308 is dimensioned and configured for receiving the longitudinal member 108. The socket 310 is dimensioned and configured to house and secure the bulbous end 112 of the bone screw 102. The hole 312 may be adapted to accommodate the neck portion 114 of the bone screw 102. Furthermore, the screw head 106 also includes external features or cuts 314 that assist in accommodating surgical instrumentation during manipulation and assembly during the surgical procedure. The external cuts 314 allow various instruments (not shown) to firmly and positively hold and manipulate the screw head 106 on one side or both sides of the screw head 106. Alternatively, the screw head 106 can be made of two separate halves (up and down half or left and right half) and could be welded closed after the bone fixator component 102 is inserted into the screw head 106.

Figure 4B:
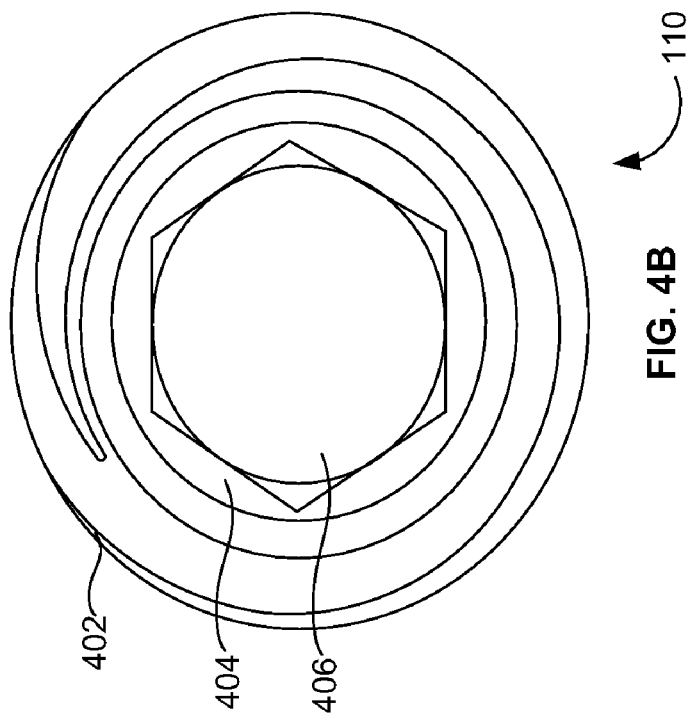
FIGS. 4A and 4B illustrate a perspective view and a front view, respectively, of a blocker of the screw assembly of FIG. 1 according to the embodiments herein.
Figure 4A:
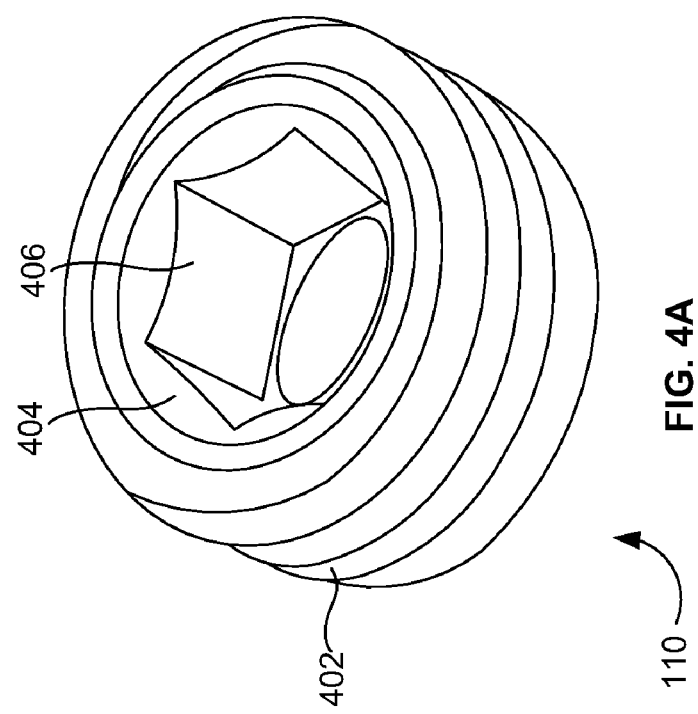

As shown in FIGS. 4A and 4B, the blocker 110 includes a thread 402 and a top 404 with a fastening feature 406. The thread 402 can be any appropriate thread configured along an outer perimeter of the blocker 110. The fastening feature 406 of the top 404 of the blocker 110 includes as a hex or square lock feature to allow high torque to be applied in locking the screw assembly 100.

The blocker 110 helps to secure the rod 108 inside the screw head 106. The threads 402 of the blocker 110 are configured to engage the threads 206 of the pair of arms 302, 304 of the screw head 106. Additionally, the blocker 110 aids in preventing the expansion of the screw head 106 when torqued on the rod 108, directing the counterforce more vertically than horizontally. Moreover, the blocker 110 may have a "timed" thread that is consistently and precisely related to the blocker 110 driving tool (not shown) to help calculate the torsional and vertical position of the blocker 110 thereby assisting the torque measurement applied to the blocker 110.

Figure 5A:
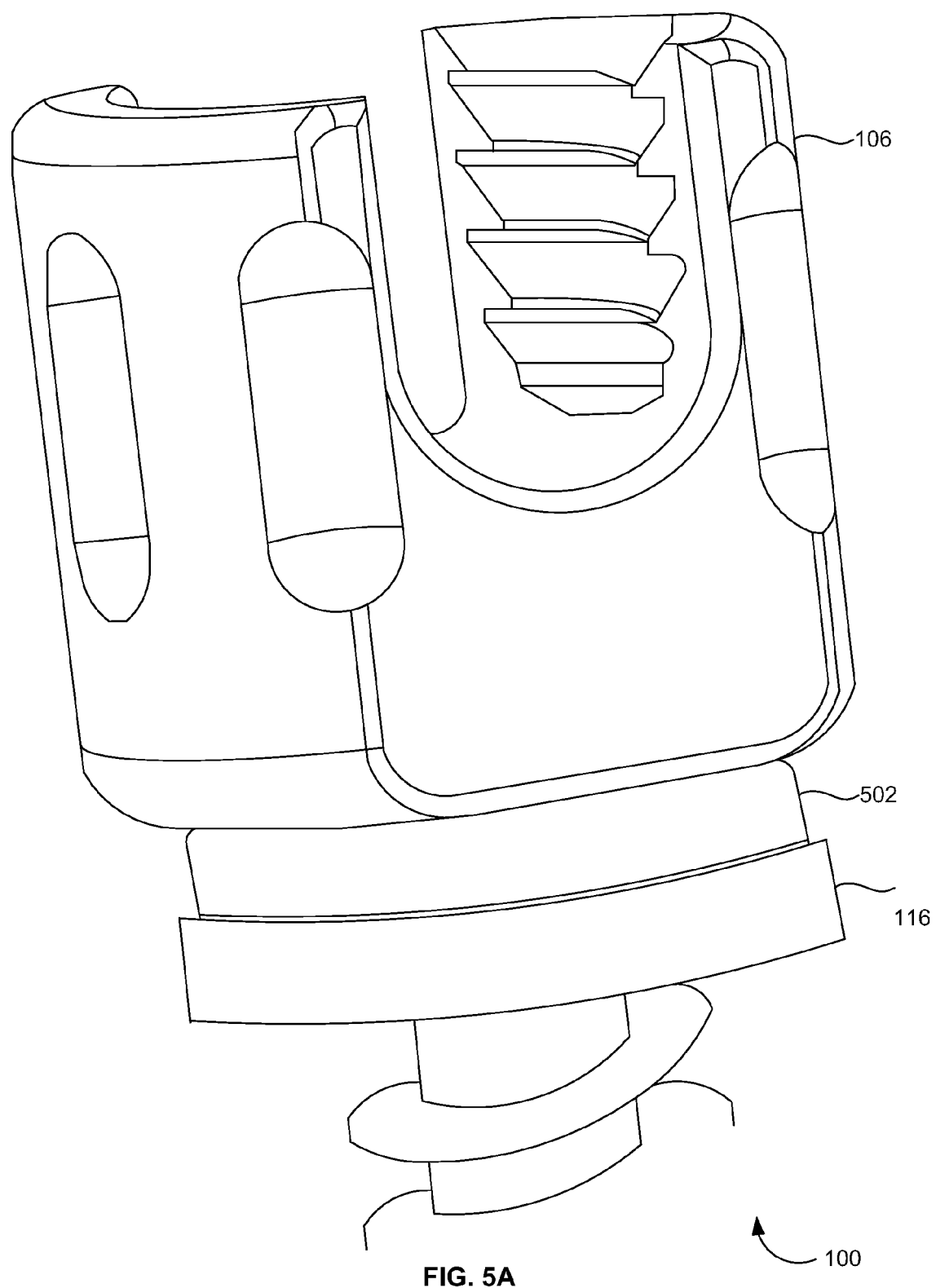
FIGS. 5A and 5B illustrate an isolated perspective view and a cross-sectional view, respectively, of the screw head and a bone screw interface according to a first embodiment herein.
Figure 5B:
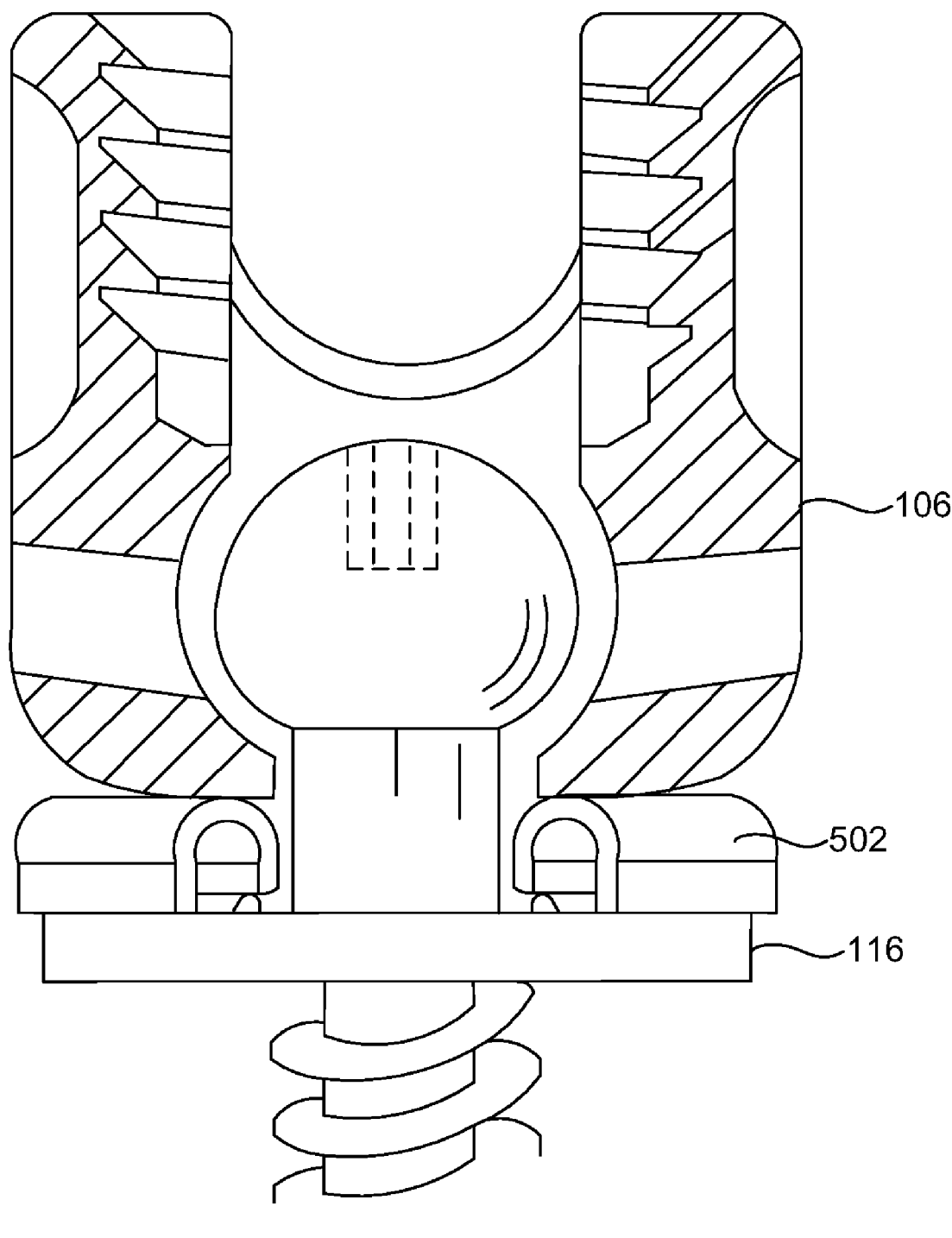

FIGS. 5A and 5B illustrate an isolated perspective view and a cross-sectional view, respectively, of the screw head 106 and the bone screw 102 interface according to a first embodiment herein. The load sharing mechanism 104 may be configured as a metallic wave/or hollowed washer 502 that could allow some structural collapse.

Figure 6A:
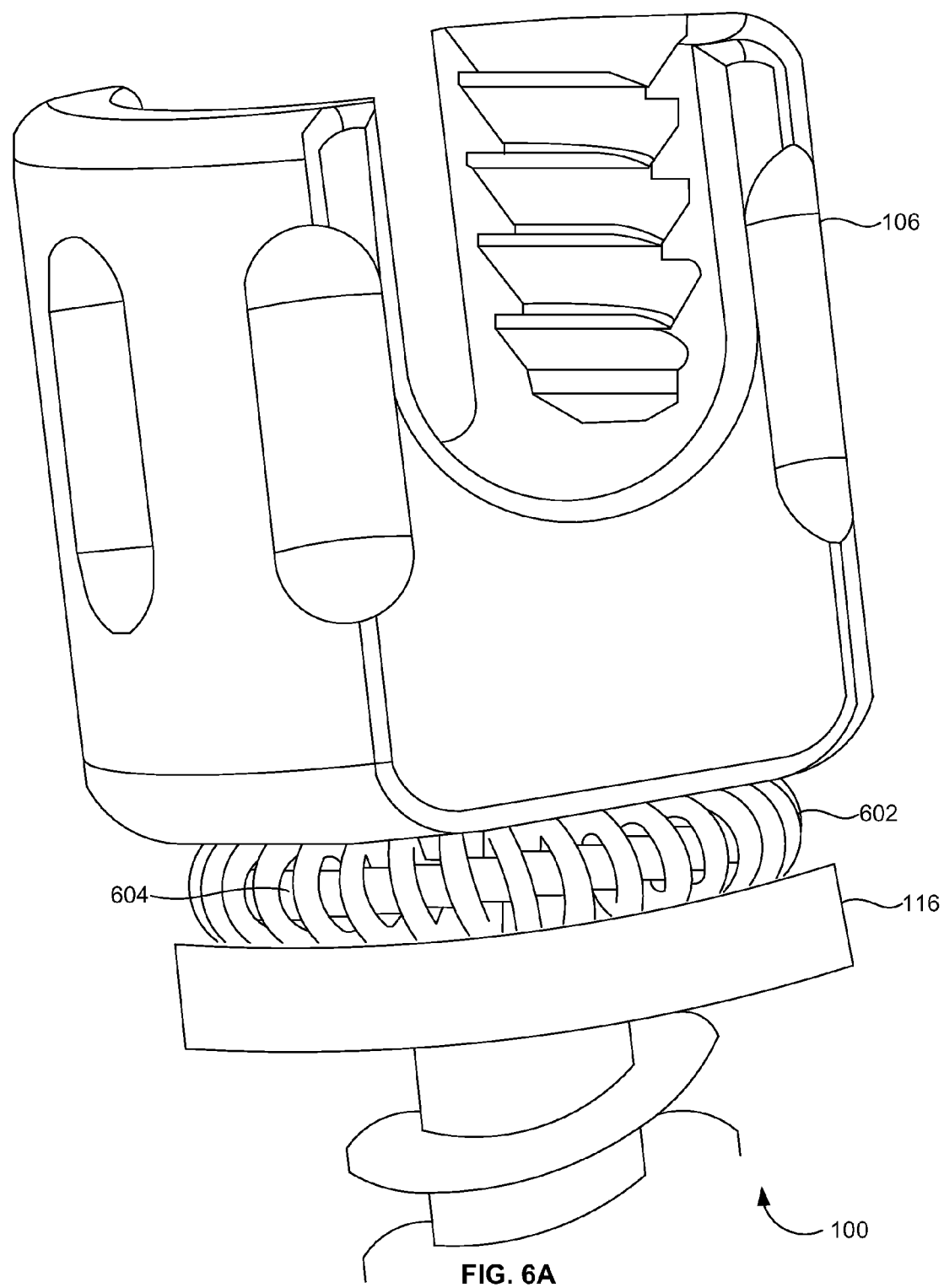
FIGS. 6A and 6B illustrate an isolated perspective view and a cross-sectional view, respectively, of the screw head and the bone screw interface according to a second embodiment herein.
Figure 6B:
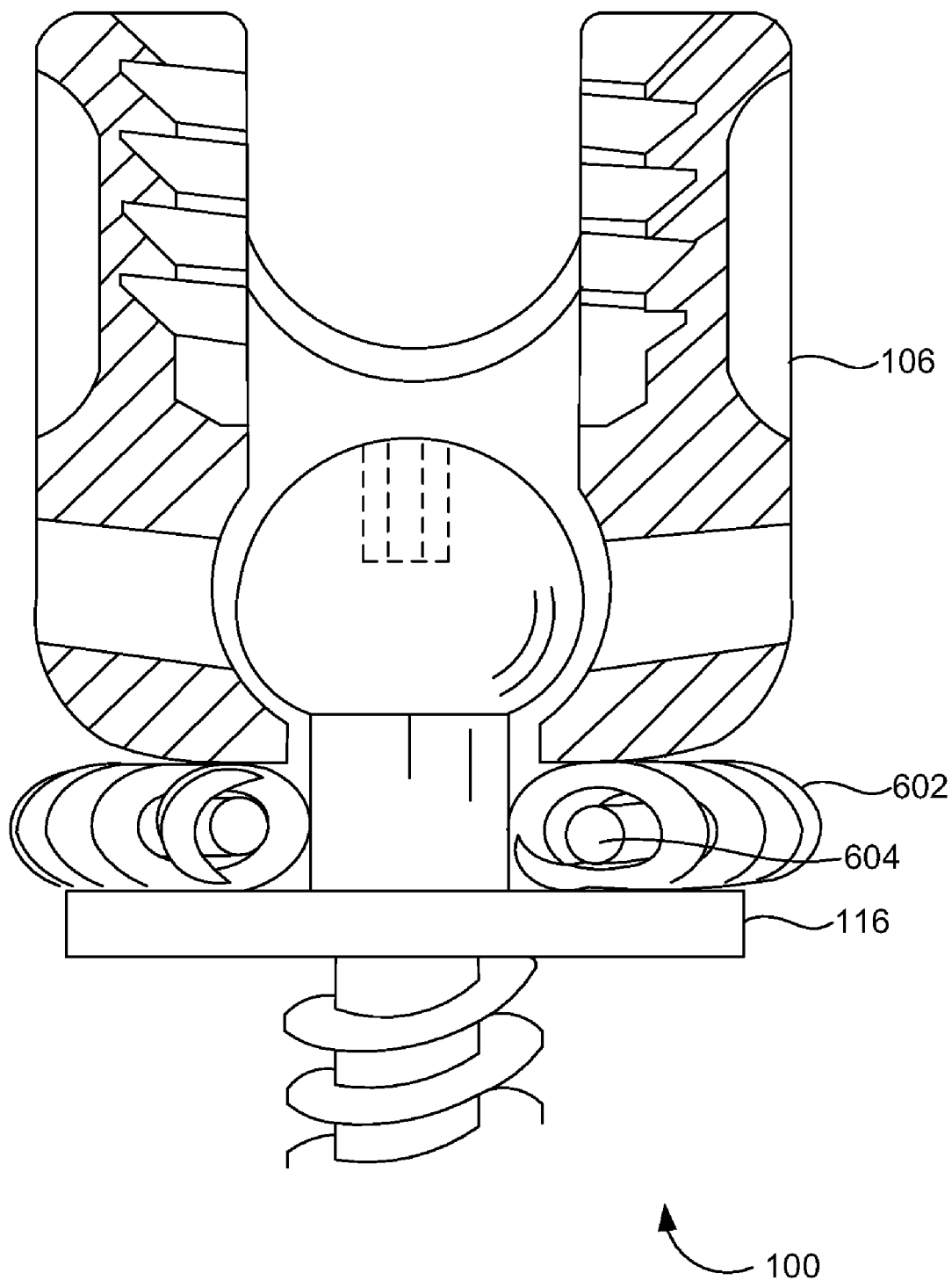

FIGS. 6A and 6B illustrate an isolated perspective view and a cross-sectional view, respectively, of the screw head, and the bone screw 102 interface according to a second embodiment herein. The load sharing mechanism 104 may be configured as a metallic coiled spring 602. The coiled spring 602 is wrapped into a full diameter and may include an interior rounded washer 604 to further limit the range of motion.

Figure 7A:
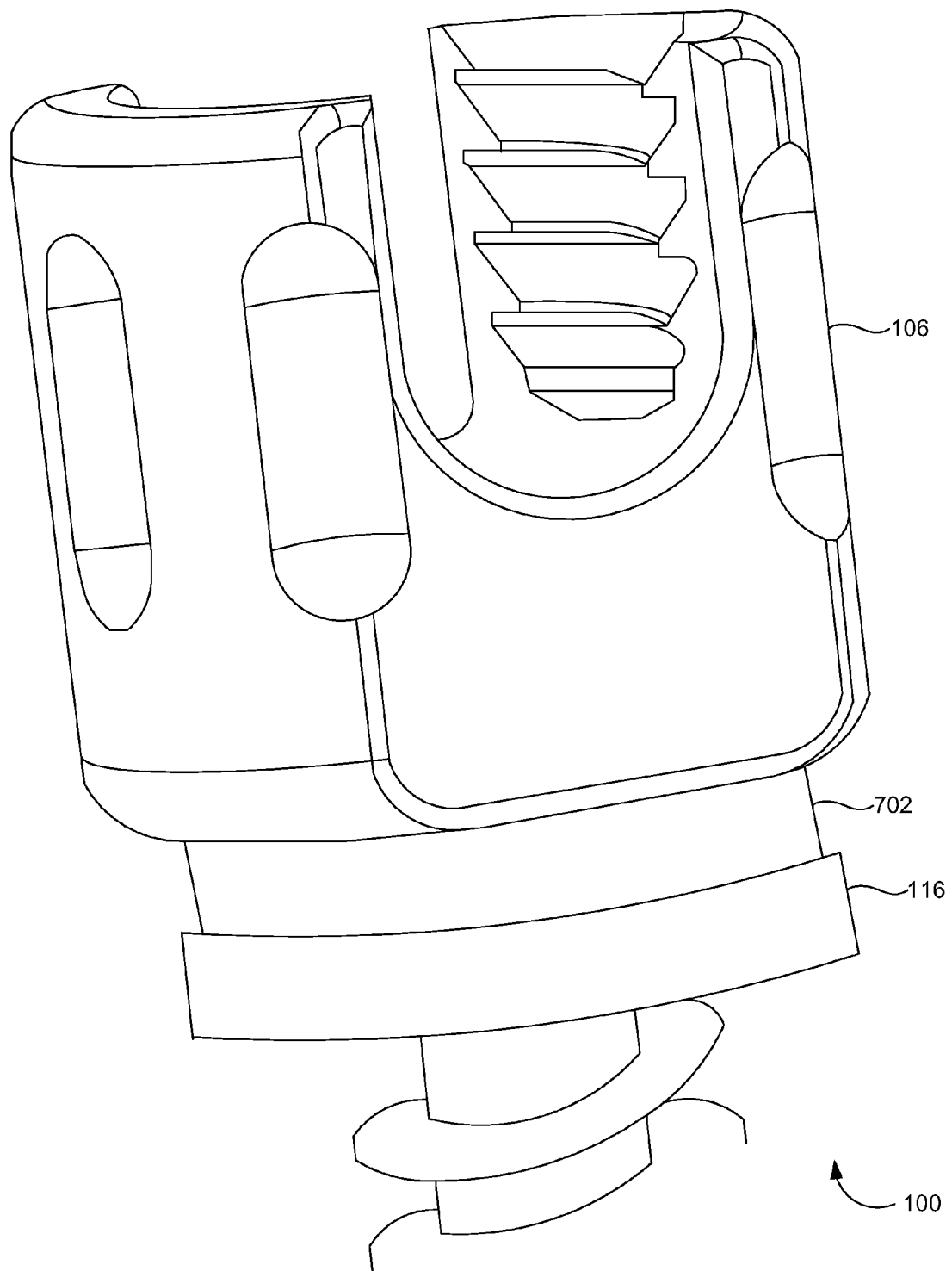
FIGS. 7A and 7B illustrate an isolated perspective view and a cross-sectional view, respectively, of the screw head and a bone screw interface according to a third embodiment herein.
Figure 7B:
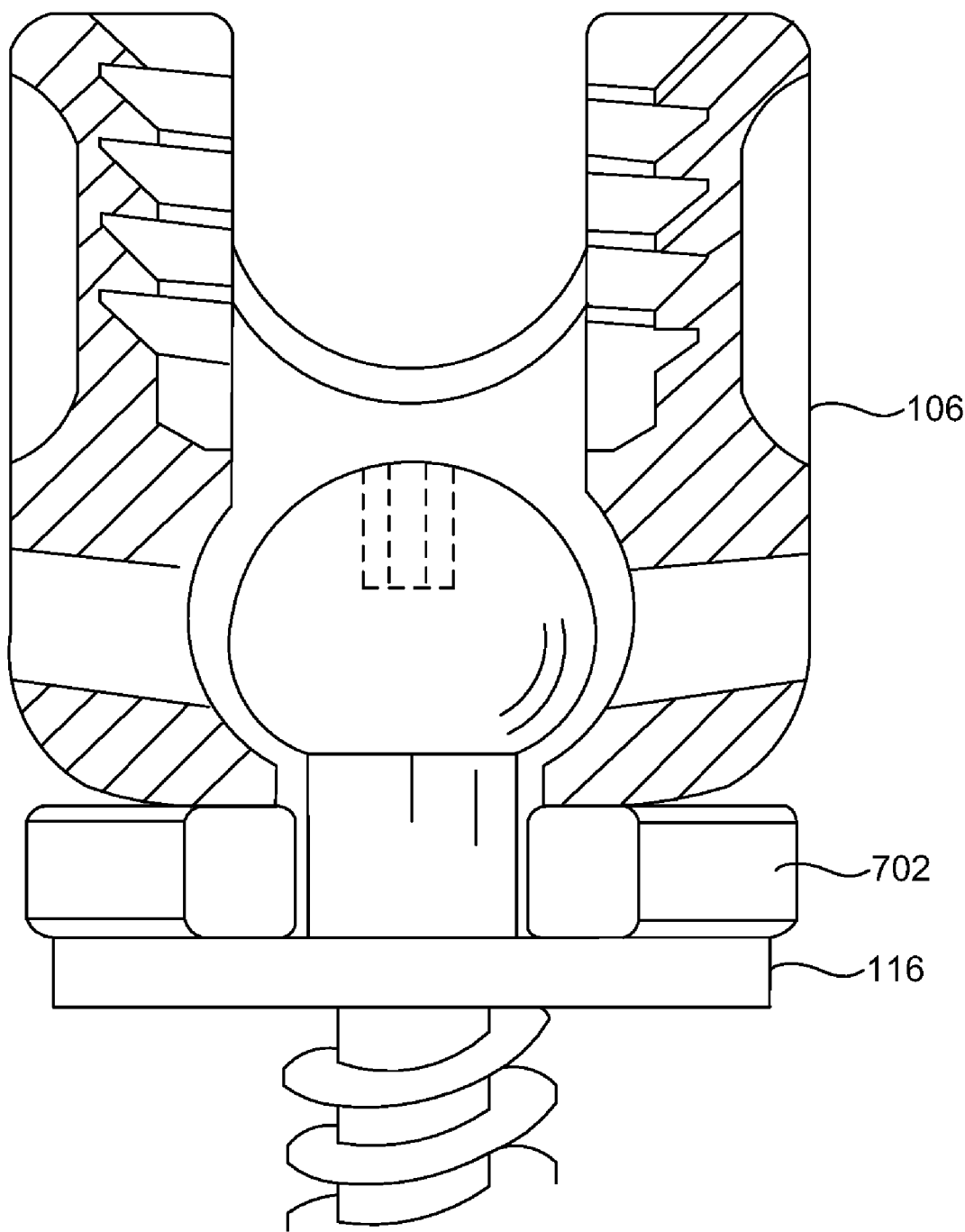

FIGS. 7A and 7B illustrate an isolated perspective view and a cross-sectional view, respectively, of the screw head and a bone screw 102 interface according to a third embodiment herein. The load sharing mechanism 104 may be configured as a flexible polymer washer 702 and may comprise silicon or urethane materials, for example.

Figure 8A:
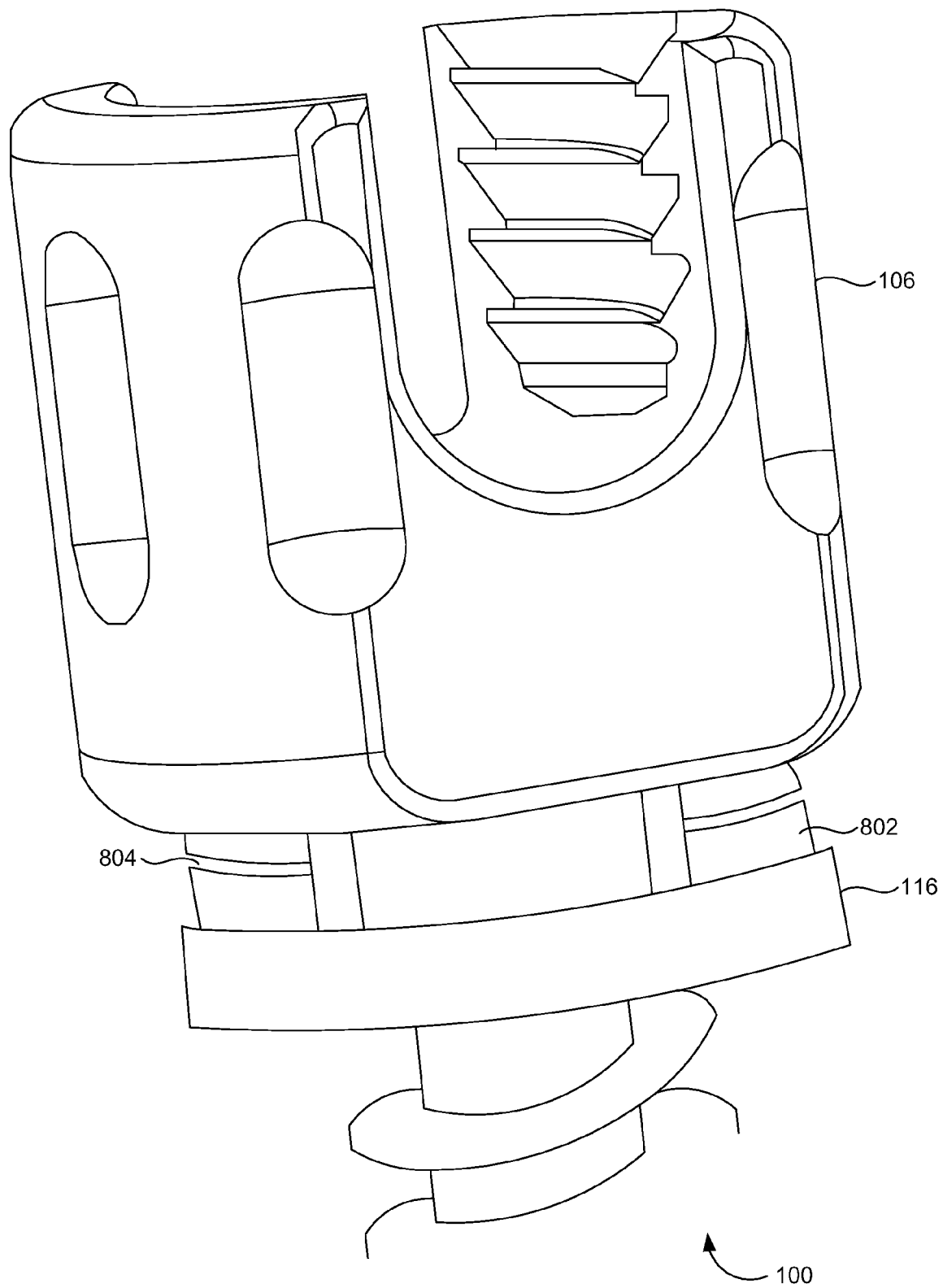
FIGS. 8A and 8B illustrate an isolated perspective view and a cross-sectional view, respectively, of the screw head and the bone screw interface according to a fourth embodiment herein.
Figure 8B:
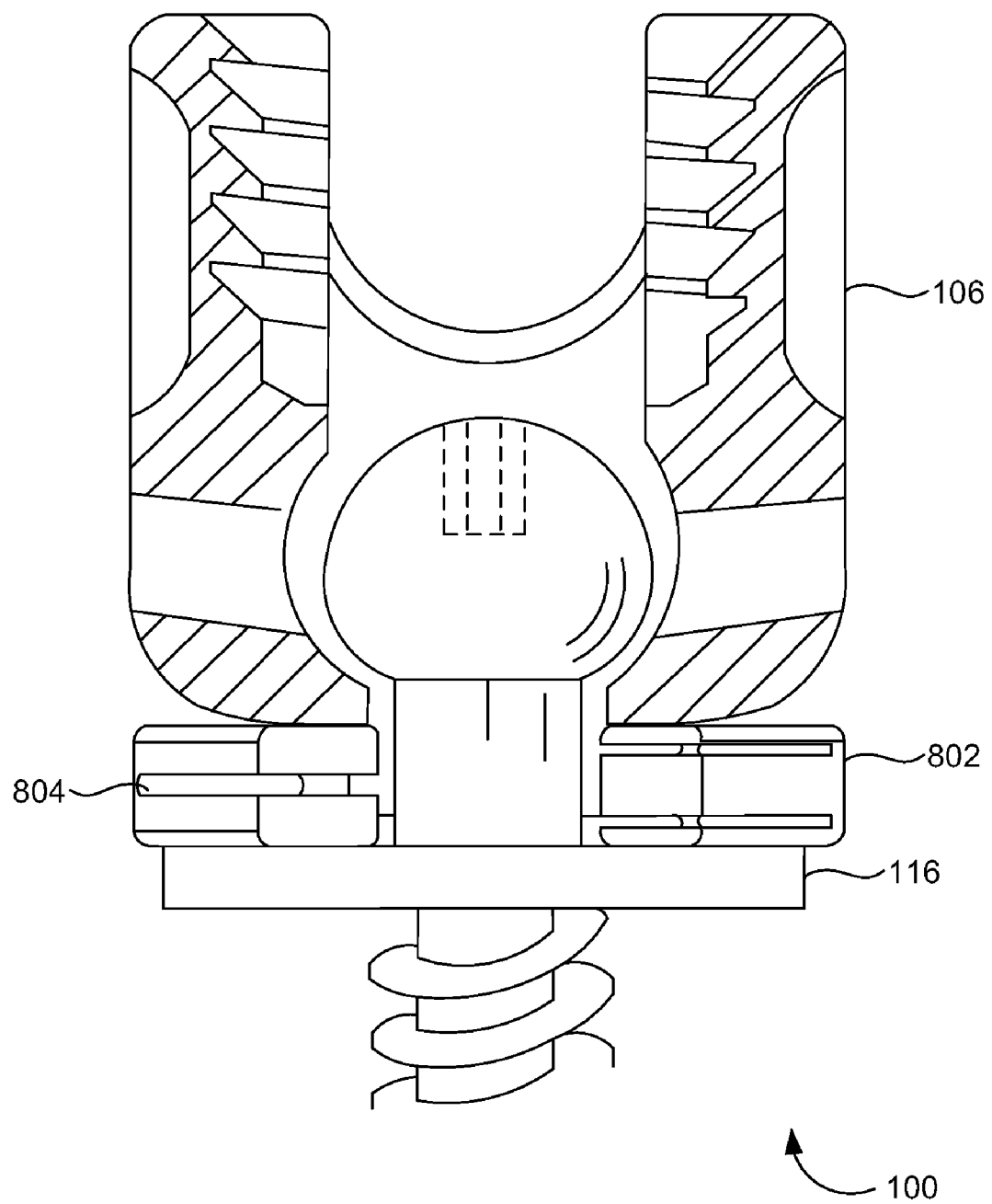

FIGS. 8A and 8B illustrate an isolated perspective view and a cross-sectional view, respectively, of the screw head 106 and the bone screw 102 interface according to a fourth embodiment herein. The load sharing mechanism 104 may be configured as a metallic washer 802. The metallic washer 802 further includes cutouts 804 that can allow some structural collapse in desired locations or directions.

FIG. 9A illustrates a perspective view of a hook 900 according to an alternate embodiment herein. FIG. 9B illustrates a perspective view of the screw assembly 100 according to the alternate embodiment herein. The hook 900 includes a bulbous end 902, a dimpled outer portion 904, a pair of arms 906, 908 connected by a connection arm 910, a space 912, and a shoulder 914. The space 912 separates the arms 906, 908 from one another. The bulbous end 902 is adapted to be inserted into the screw head 106. The arms 906, 908 are configured to receive an additional member (not shown) for subsequent attachment to the bone. The shoulder 914 is dimensioned and configured to accommodate the load sharing mechanism 104.

Figure 10:
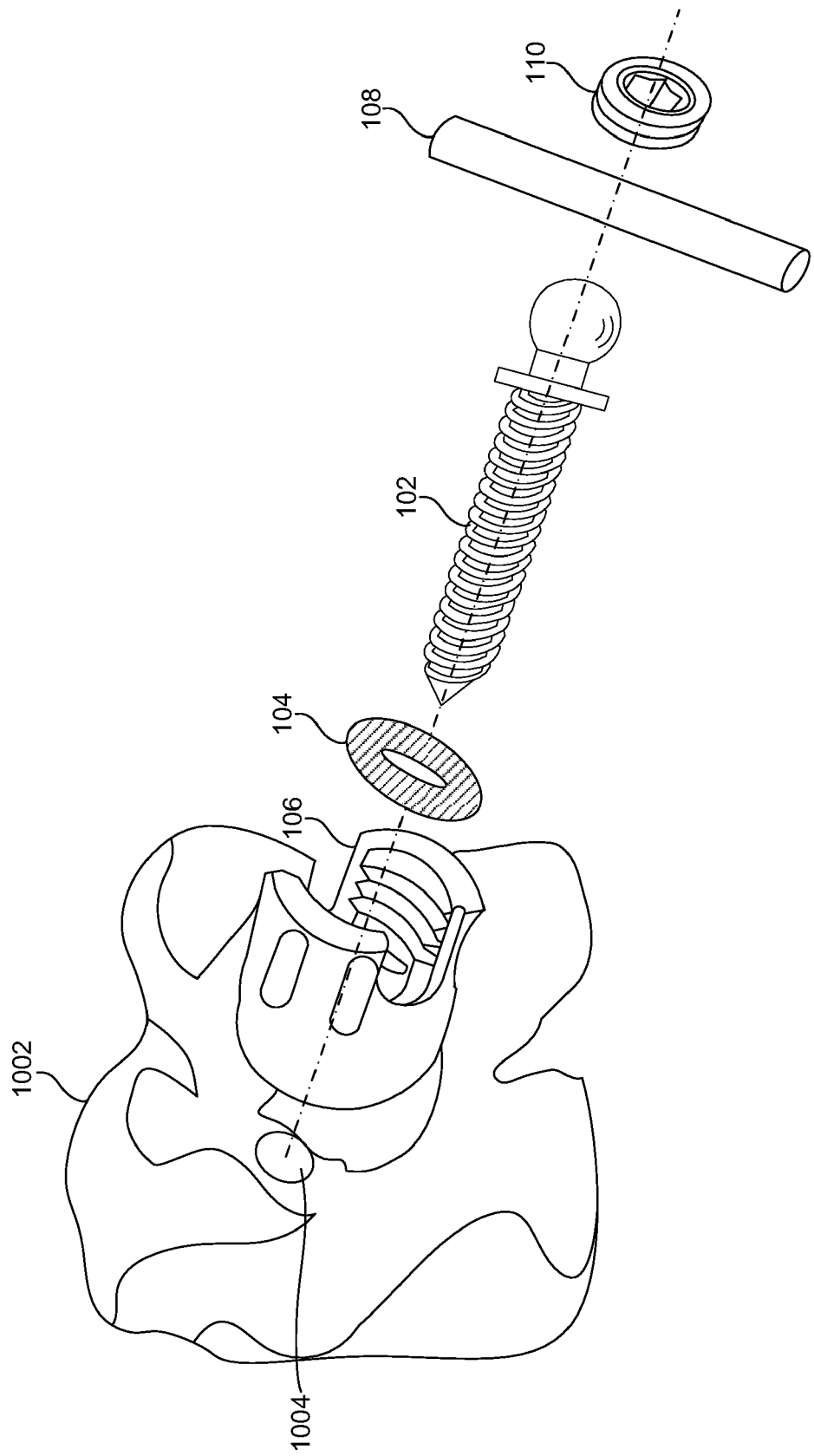
FIG. 10 illustrates a cross-sectional view of a vertebrae showing implantation of the screw assembly of FIGS. 1 and 2A according to the embodiments herein.

FIG. 10, with respect to FIGS. 1 through 9B, illustrates a cross-sectional view of a vertebrae 1002 showing implantation of the screw assembly 100 of FIG. 1 according to the embodiments herein. For the implantation of the screw assembly 100 in the vertebrae 1002, initially, an area of implantation is surgically approached and an incision 1004 is made over the spine. The shoulder mechanism 116 and the load sharing mechanism 104 are positioned around the neck portion 114 of the bone screw 102. After the incision 1004 has been created, the screw head 106 is inserted into the incision 1004. Then the bone screw 102 (with the load sharing mechanism 104 and the shoulder mechanism 116) is inserted into the screw head 106. An appropriate length of the rod 108 is chosen and inserted into the U-shaped slot 308 of the bone screw 102. Finally, the blocker 110 is introduced into the threaded inner portion 306 of the screw head 106. This may be accomplished by using a hexagonal screwdriver (not shown).

Moreover, according to an aspect of the embodiments herein, the screw assembly 100 can be used as a dynamic rod system to complement artificial discs. The embodiments herein provide an implantable pedicle screw assembly 100 that has the shoulder mechanism 116 positioned around the neck portion 114 of the bone screw 102, which is as wide as the bulbous end 112 of the bone screw 102 and provides support to the bone screw 102 and the screw head 106. Additionally, as the rod 108 does not contact the bone screw 102, it offers the surgeon more lateral range of motion by providing a larger arc of rotation. Moreover, the assembly 100 includes the load sharing mechanism 104 adapted to allow the screw head 106 to have an increased tensile load, and such that the assembly 100 may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An assembly comprising:
   a monolithic fixator component comprising a bulbous end, a neck portion, and a threaded end;
   a smooth, cylindrically shaped clamping mechanism around said neck portion of said fixator component;
   a screw head comprising:
      a pair of diametrically opposed arms;
      a socket positioned between said pair of arms and dimensioned and configured to house said bulbous end of said fixator component; and
      a slot positioned above said socket and between said pair of arms;
   a load sharing mechanism positioned in between said screw head and said clamping mechanism around said neck portion of said fixator component, wherein said load sharing mechanism provides tensile resistance to said screw head; and
   a blocker adapted to engage said screw head.

2. The assembly of claim 1, wherein said slot is dimensioned and configured for receiving a longitudinal member.

3. The assembly of claim 2, wherein said fixator component is spaced apart from said longitudinal member.

4. The assembly of claim 1, wherein said fixator component comprises a bone screw.

5. The assembly of claim 1, wherein said fixator component comprises a hook.

6. The assembly of claim 1, wherein said load sharing mechanism comprises a washer.

7. The assembly of claim 1, wherein said load sharing mechanism comprises a hole.

8. The assembly of claim 1, wherein said clamping mechanism is detachable.

9. The assembly of claim 1, wherein said clamping mechanism comprises a width greater than a width of said bulbous end of said fixator component.

10. A pedicle fixation assembly comprising:
    a monolithic bone screw comprising a spherical end, a neck portion, and a threaded end;
    a smooth, cylindrically shaped shoulder mechanism positioned around said neck portion of said bone screw;
    a screw head comprising:
       a pair of threaded upright arms;
       a socket positioned between the pair of arms and dimensioned and configured to secure said bulbous end of said bone screw;
       a slot positioned at a first end of said screw head and between said pair of arms; and
       a hole adjacent to said socket and positioned at a second end of said screw head;
    a load sharing mechanism positioned in between said screw head and said shoulder mechanism around said neck portion of said bone screw, wherein said load sharing mechanism provides tensile resistance to said screw head; and
    a threaded blocker mechanism adapted to engage threads of said pair of arms of said screw head.

11. The assembly of claim 10, wherein said slot is dimensioned and configured for receiving a longitudinal member.

12. The assembly of claim 11, wherein said bone screw is spaced apart from said longitudinal member.

13. The assembly of claim 10, wherein said load sharing mechanism comprises a washer.

14. The assembly of claim 10, wherein said load sharing mechanism comprises a hole.

15. The assembly of claim 10, wherein said shoulder mechanism is detachable.

16. The assembly of claim 10, wherein said shoulder mechanism comprises a width equal to a width of said bulbous end of said bone screw.

17. An apparatus comprising:
   a monolithic bone screw comprising a bulbous end, a neck portion, and a threaded end;
   a shank structure positioned completely around said neck portion of said bone screw and detachable from said neck portion of said bone screw, wherein said shank structure comprises a width at least equal to a width of said bulbous end of said bone screw;
   a screw head comprising:
      a pair of threaded upright arms;
      a socket positioned between the pair of arms and dimensioned and configured to secure said bulbous end of said bone screw;
      a slot positioned at a first end of said screw head and between said pair of arms; and
      a hole adjacent to said socket and positioned at a second end of said screw head;
   a load sharing mechanism positioned in between said screw head and said shank structure around said neck portion of said bone screw, wherein said load sharing mechanism provides tensile resistance to said screw head;
   a longitudinal member positioned in said slot of said screw head, wherein said bone screw does not contact said longitudinal member; and
   a threaded blocker mechanism adapted to engage the threads of said pair of arms of said screw head and secure said longitudinal member in said slot.

18. The apparatus of claim 17, wherein said longitudinal member comprises a length and a width, wherein said length is substantially greater than said width.

19. The apparatus of claim 17, wherein said load sharing mechanism comprises a washer.

20. The apparatus of claim 17, wherein said load sharing mechanism comprises a hole.

* * * * *